United States Patent
Sahin et al.

(10) Patent No.: US 11,510,943 B2
(45) Date of Patent: Nov. 29, 2022

(54) CHEMOTHERAPEUTIC AGENT COMPRISING COMBINATION OF ALEXIDINE DIHYDROCHLORIDE AND SODIUM PENTABORATE PENTAHYDRATE

(71) Applicant: YEDITEPE UNIVERSITESI, Istanbul (TR)

(72) Inventors: Fikrettin Sahin, Istanbul (TR); Ezgi Kasikci, Istanbul (TR); Esra Aydemir Coban, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 117 days.

(21) Appl. No.: 16/980,436

(22) PCT Filed: Mar. 11, 2019

(86) PCT No.: PCT/TR2019/050152
§ 371 (c)(1),
(2) Date: Sep. 14, 2020

(87) PCT Pub. No.: WO2020/018037
PCT Pub. Date: Jan. 23, 2020

(65) Prior Publication Data
US 2021/0015854 A1    Jan. 21, 2021

(30) Foreign Application Priority Data
Mar. 12, 2018 (TR) .................. 2018/03493

(51) Int. Cl.
*A61K 33/22* (2006.01)
*A61P 35/00* (2006.01)
*A61K 31/155* (2006.01)

(52) U.S. Cl.
CPC ............ *A61K 33/22* (2013.01); *A61K 31/155* (2013.01); *A61P 35/00* (2018.01)

(58) Field of Classification Search
CPC ... A61K 31/155; A61K 33/22; A61K 2300/00
See application file for complete search history.

(56) References Cited

U.S. PATENT DOCUMENTS 9,399,032 B2    7/2016    Mootha et al.

FOREIGN PATENT DOCUMENTS

| WO | 2005060951 A2 | 7/2005 | |
| WO | 2014200447 A1 | 12/2014 | |
| WO | WO-2014200447 A1 * | 12/2014 | ............. A61K 31/69 |

OTHER PUBLICATIONS

Yip et al (Molecular Cancer Therapeutics, 2006, vol. 5, pp. 2234-2240). (Year: 2006).*

Mehmet Korkmaz et al, Disodium pentaborate decahydrate (DPD) induced apoptosis by decreasing hTERT enzyme activity and disrupting F-actin organization of prostate cancer cells, Tumor Biology, 2013, Springer.

Selami Demirci, et al., Boron promotes streptozotocin-induced diabetic wound healing: roles in cell proliferation and migration, growth factor expression, and inflammation, Mol Cell Biochem, 2016, pp. 119-133, vol. 417, Springer.

David Katz et al. Increased efficiency for performing colony formation assays in 96-well plates: novel applications to combination therapies and high-throughput screening, BioTechniques for Preclinical Development, 2008, pp. ix-xiv, vol. 44 No. 2.

Kenneth W. Yip, et al., Potential use of alexidine dihydrochloride as an apoptosis-promoting anticancer agent, Molecular Cancer Therapeutics, 2006, pp. 2234-2240, vol. 5 No. 9.

* cited by examiner

*Primary Examiner* — Mark V Stevens
(74) *Attorney, Agent, or Firm* — Bayramoglu Law Offices LLC

(57) ABSTRACT

The present invention relates to a chemotherapeutic agent comprising a combination of alexidine dihydrochloride and sodium pentaborate pentahydrate. The chemotherapeutic agent includes 2.9 mg alexidine dihydrochloride compound and 2.5 mg sodium pentaborate pentahydrate compound, and is obtained by adding 0.5 ml dimethylsulfoxide compound into the alexidine dihydrochloride compound. Upon injecting them to the media containing healthy cells and cancer cells, their effects on cell viability were observed. In accordance with the obtained results; it was observed that when alexidine dihydrochloride solution at concentrations not harming healthy cells is combined with sodium pentaborate pentahydrate, pancreatic cancer cell viability decreased 10% more compared to use of alexidine dihydrochloride alone, and it was realized that this combination can be used as a chemotherapeutic agent for treatment of pancreatic cancer.

8 Claims, 8 Drawing Sheets

Figure 1:
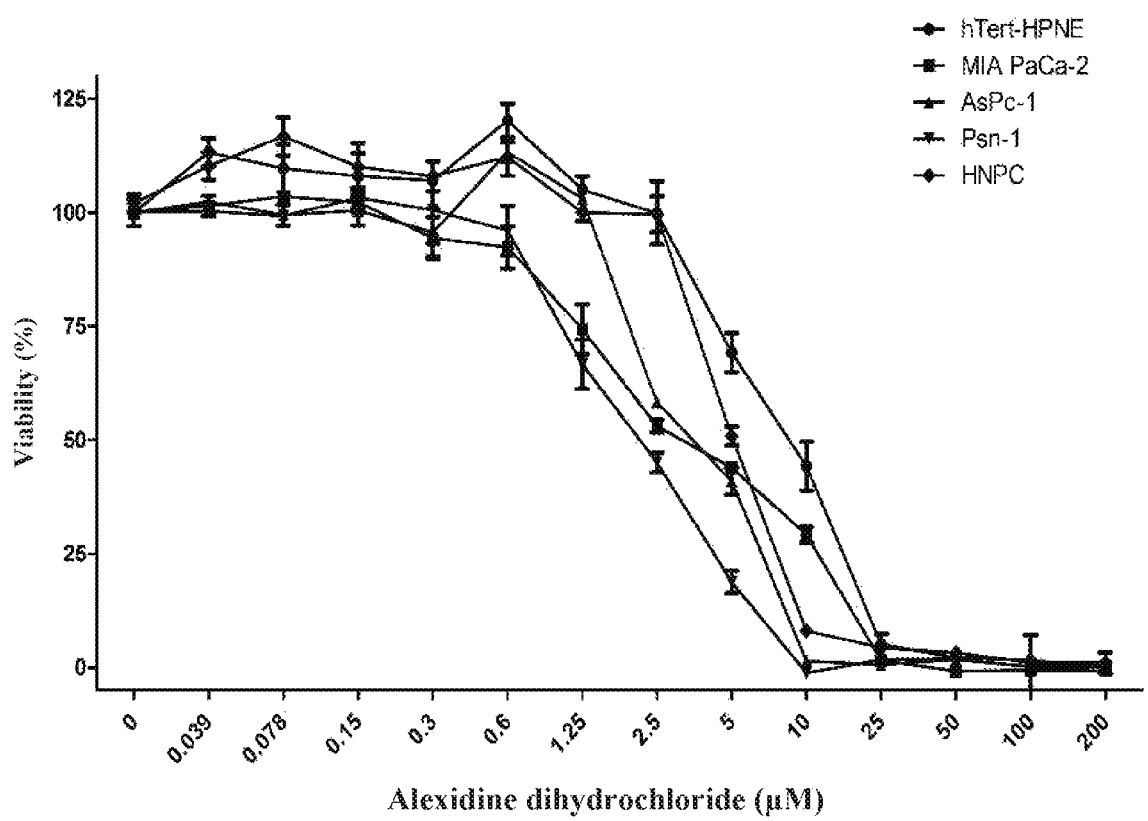

CHEMOTHERAPEUTIC AGENT COMPRISING COMBINATION OF ALEXIDINE DIHYDROCHLORIDE AND SODIUM PENTABORATE PENTAHYDRATE

CROSS REFERENCE TO THE RELATED APPLICATIONS

This application is the national phase entry of International Application No. PCT/TR2019/050152, filed on Mar. 11, 2019, which is based upon and claims priority to Turkey Patent Application No. 2018/03493, filed on Mar. 12, 2018, the entire contents of which are incorporated herein by reference.

FIELD OF THE INVENTION

The present invention relates to the effect of the combination of alexidine dihydrochloride and sodium pentaborate pentahydrate on pancreatic cancer.

BACKGROUND OF THE INVENTION

The pancreas is an organ which is approximately 15 cm long and located in the rearmost part of the abdomen, and whose front surface is completely covered with the stomach, duodenum and large intestine. It is known that pancreatic cancer has the least response to treatment among cancer types. The pessimistic predictions about the results of the surgical treatment of pancreatic cancer left their place to relatively better results after the eighties.

Although the etiology in pancreatic cancer is not known exactly, some risk factors have been identified. These are factors such as: age (increased risk after age 50), gender (increased risk of pancreatic cancer in men), smoking (30% of pancreatic cancer cases are thought to be associated with smoking), diet (it is difficult to formulate an idea about diet and exercise, however it is considered that consumption of fruits, vegetables, and fiber food reduce the risk, while consumption of meat and fatty products increase it).

The exact location of the tumor in the pancreas, the stage of the disease, the physical state of the patient (age, weight, etc.) are evaluated for the treatment of pancreatic cancer; and then one or more selected from the methods of surgical treatment, radiotherapy and chemotherapy is/are used.

Chemotherapy is the use of anti-cancer drugs to kill cancer cells. Pancreatic cancers can be treated with drug treatment called chemotherapy taking into consideration the general conditions of the patients before and after surgery. Chemotherapy can be applied to shrink tumors prior to surgery or as a primary treatment in combination with radiotherapy in place of surgery. Surgery and radiotherapy are not useful in advanced stage spread disease. It is known that the patients' quality of life can be significantly improved by applying chemotherapy to this group of patients.

The United States patent document no. U.S. Pat. No. 9,399,032B2, known in the art, discloses that a group of chemicals, including alexidine dihydrochloride, selectively inhibits cell growth upon being dissolved in galactose.

It is disclosed in the abstract of the article titled "Potential use of alexidine dihydrochloride as an apoptosis-promoting anticancer agent" in the book named Molecular Cancer Therapeutics published by Kenneth W. Yip, Emma Ito, Xinliang Mao, P. Y. Billie Au, David W. Hedley, Joseph D. Mocanu, Carlo Bastianutto, Aaron Schimmer and Fei-Fei Liu published on September 2006, that alexidine dihydrochloride is used for cancer treatment.

It is disclosed in the article titled "Increased efficiency for performing colony formation assays in 96-well plates: novel applications to combination therapies and high-throughput screening" in the book named Bio Techniques published on February 2008 by David Katz, Emma Ito, Ken S. Lau, Joseph D. Mocanu, Carlo Bastianutto, Aaron D. Schimmer, and Fei-Fei Liu, that alexidine dihydrochloride can be used in anti-cancer applications.

SUMMARY OF THE INVENTION

The objective of the present invention is to increase the therapeutic effect of the product produced by adding sodium pentaborate pentahydrate to the alexidine dihydrochloride compound by 10 to 20%.

Another objective of the present invention is to use the combination of alexidine dihydrochloride and sodium pentaborate pentahydrate as a chemotherapeutic agent for pancreatic cancer treatment.

DETAILED DESCRIPTION OF THE INVENTION

The present invention is a chemotherapeutic agent which is used in pancreatic cancer treatment and is obtained by the following steps:
  weighing 2.9 mg of alexidine dihydrochloride compound,
  preparing alexidine dihydrochloride solution with concentrations of 200 µM, 100 µM, 50 µM, 25 µM, 10 µM, 5 µM, 2.5 µM, 1.25 µM, 0.6 µM, 0.3 µM, 0.15 µM, 0.078 µM and 0.039 µM respectively by adding dimethylsulfoxide solution into alexidine dihydrochloride,
  adding the solutions separately into the medium containing pancreatic cancer cells (MIA PaCa-2, AsPc-1 and Psn-1), pancreatic healthy cells (hTert-HPNE) and healthy intervertebral disc cells (HNPC) such that dimethylsulfoxide ratio is less than 1/1000,
  incubating at 24, 48 and 72 hours respectively in incubators with 85% moisture at a temperature of 37° C. which are the normal cell culture conditions,
  performing colorimetric tetrazolium salt (MTS) viability assay,
  preparing 2.5 µM alexidine dihydrochloride incubated at 48 hours which is determined in the light of the results of the analysis to give the optimum result,
  preparing sodium pentaborate pentahydrate solutions at concentrations of 1000 µM, 500 µM, 250 µM, 100 µM, respectively,
  applying the prepared sodium pentaborate pentahydrate solutions to the media of pancreatic healthy cells (hTert-HPNE), healthy intervertebral disc cells (HNPC), human foreskin mesenchymal stem cells (hFSSCs), human umbilical vein endothelial cells (HUVEC) and pancreatic cancer cells (MIA PaCa-2, AsPc-1 and Psn-1) in incubators with 85% moisture at a temperature of 37° C. which are the normal cell culture conditions,
  performing colorimetric tetrazolium salt (MTS) viability assay in the medium containing sodium pentaborate pentahydrate solutions and the cells,
  preparing sodium pentaborate pentahydrate solutions at concentrations of 1000 µM, 500 µM, 250 µM, 100 µM, respectively, and applying them together with alexidine dihydrochloride to the media containing pancreatic healthy cells (hTert-HPNE), healthy intervertebral disc cells (HNPC), human foreskin mesenchymal stem cells (hFSSCs), human umbilical vein endothelial cells (HUVEC) and pancreatic cancer cells (MIA PaCa-2, AsPc-1 and Psn-1) respectively in incubators with 85% moisture at a temperature of 37° C. which are the normal cell culture conditions, performing colorimetric tetrazolium salt (MTS) viability assay in the medium containing solutions of alexidine dihydrochloride and sodium pentaborate pentahydrate solutions and the cells.

The chemotherapeutic agent of the present invention comprises a combination of alexidine dihydrochloride and sodium pentaborate pentahydrate and induces apoptosis on pancreatic cancer cells. Alexidine dihydrochloride is a compound having a molecular weight of 581.71 gram/mol and the chemical formula of $C_{26}H_{56}N_{10} \cdot 2HCl$ and it is dissolved in dimethylsulfoxide of 10 mg/ml or above. The effective dose of alexidine dihydrochloride on pancreatic cancer is determined by conducting colorimetric tetrazolium salt (MTS) viability assay on pancreatic cancer cells (MIA PaCa-2, AsPc-1 and Psn-1), pancreatic healthy cells (hTert-HPNE) and healthy intervertebral disc cells (HNPC).

Alexidine dihydrochloride was dissolved in dimethylsulfoxide to prepare an alexidine dihydrochloride solution at concentrations of 200 μM, 100 μM, 50 μM, 25 μM, 10 μM, 5 μM, 2.5 μM, 1.25 μM, 0.6 μM, 0.3 μM, 0.15 μM, 0.078 μM and 0.039 μM; and was added to the medium containing pancreatic cancer cells (MIA PaCa-2, AsPc-1 and Psn-1), pancreatic healthy cells (hTert-HPNE) and healthy intervertebral disc cells (HNPC) such that dimethylsulfoxide ratio is less than 1/1000. As a result of the colorimetric tetrazolium salt (MTS) viability assay performed after incubation of 72 hours, it was determined that the healthy pancreas cell and the healthy intervertebral disc cells were not affected, however viability of the pancreatic cancer cells was reduced to 50% by 2.5 μM which is the median toxic dose (TD50) and 48 hours of incubation.

In order to increase the chemotherapeutic effect of the alexidine dihydrochloride solution, it is planned to add sodium pentaborate pentahydrate compound to the solution. Sodium pentaborate pentahydrate is a compound having a molecular weight of 295.107 grams/mol and the chemical formula of $B_5H_{10}NaO_{13}$.

The sodium pentaborate pentahydrate compound was dissolved in the appropriate medium for the cell that was used and filtered to enable sterilization. Sodium pentaborate pentahydrate compound at concentrations used is dissolved instantly in the medium without requiring any additional solvent addition. The normal pH value of the medium was 7.4 and did not form sodium pentaborate pentahydrate precipitate for 72 hours. Then, sodium pentaborate pentahydrate was prepared at concentrations of 1000 μM, 500 μM, 250 μM, 100 μM, respectively, and was injected to the medium containing the pancreatic healthy cell (hTert-HPNE), healthy intervertebral disc cell (HNPC), human foreskin mesenchymal stem cell (hFSSCs) and human umbilical vein endothelial cell (HUVEC), and then was incubated for 48 hours. Then toxicity analysis (colorimetric tetrazolium salt (MTS) viability assay) was performed. The solution of sodium pentaborate pentahydrate at a concentration of 1000 μM incubated for 48 hours gave the optimum result with an average vitality of 70%.

Then, 2.5 μM alexidine dihydrochloride was added into the sodium pentaborate pentahydrate solution prepared at concentrations of 1000 μM, 500 μM, 250 μM, 100 μM, respectively, and was injected to the medium containing the pancreatic healthy cell (hTert-HPNE), healthy intervertebral disc cell (HNPC), human foreskin mesenchymal stem cell (hFSSCs) and human umbilical vein endothelial cell (HUVEC), and then was incubated for 48 hours. Then toxicity analysis (colorimetric tetrazolium salt (MTS) viability assay) was performed. As a result of the analysis, it was determined that the optimum combination result that does not harm the healthy cells are the combinations of 250 μM and 100 μM sodium pentaborate pentahydrate and 2.5 μM alexidine dihydrochloride.

Upon preparing solutions of the same concentration, adding them to the medium containing pancreatic cancer cells (MIA PaCa-2, AsPc-1 and Psn-1) and performing colorimetric tetrazolium (MTS) vitality assay; it was observed that the combination of 250 μM sodium pentaborate pentahydrate and 2.5 μM alexidine dihydrochloride, which is the non-lethal dose for the healthy cells, decreased the viability of pancreatic cancer cells by more than 50% upon 48 hours of incubation. This value is 10-20% more than the chemotherapeutic effect of alexidine dihydrochloride alone.

It was observed that the solution of alexidine dihydrochloride and sodium pentaborate pentahydrate prepared in the medium started to lose its effect at 4° C., at periods of time longer than 72 hours. The solution should be freshly prepared and used at once as a chemotherapeutic agent.

Experimental Analysis Data

In the graphs showing experimental analysis data, "NAB" is used as the abbreviation for sodium pentaborate pentahydrate and "AD" is used as the abbreviation for alexidine dihydrochloride. Negative control is abbreviated as "NC" and denotes that the cell's medium is used alone.

FIG. 1 shows the graph indicating the effect of alexidine dihydrochloride on the viability of healthy cells and pancreatic cancer cells (colorimetric tetrazolium (MTS) viability assay).

In the related graph; viabilities of the healthy pancreatic cells (hTert-HPNE), healthy intervertebral disc cells (HNPC) and pancreatic cancer cells (MIA PaCa-2, AsPc-1 and Psn-1) incubated for 48 hours with AD were analyzed. In the light of the results obtained; it was observed that 48-hour incubation with AD at a concentration of 2.5 μM did not harm the healthy cells, however decreased the viability of the pancreatic cancer cells to 53% for MIA PaCa-2, 58% for AsPc-1 and 45% for Psn-1.

Figure 2:
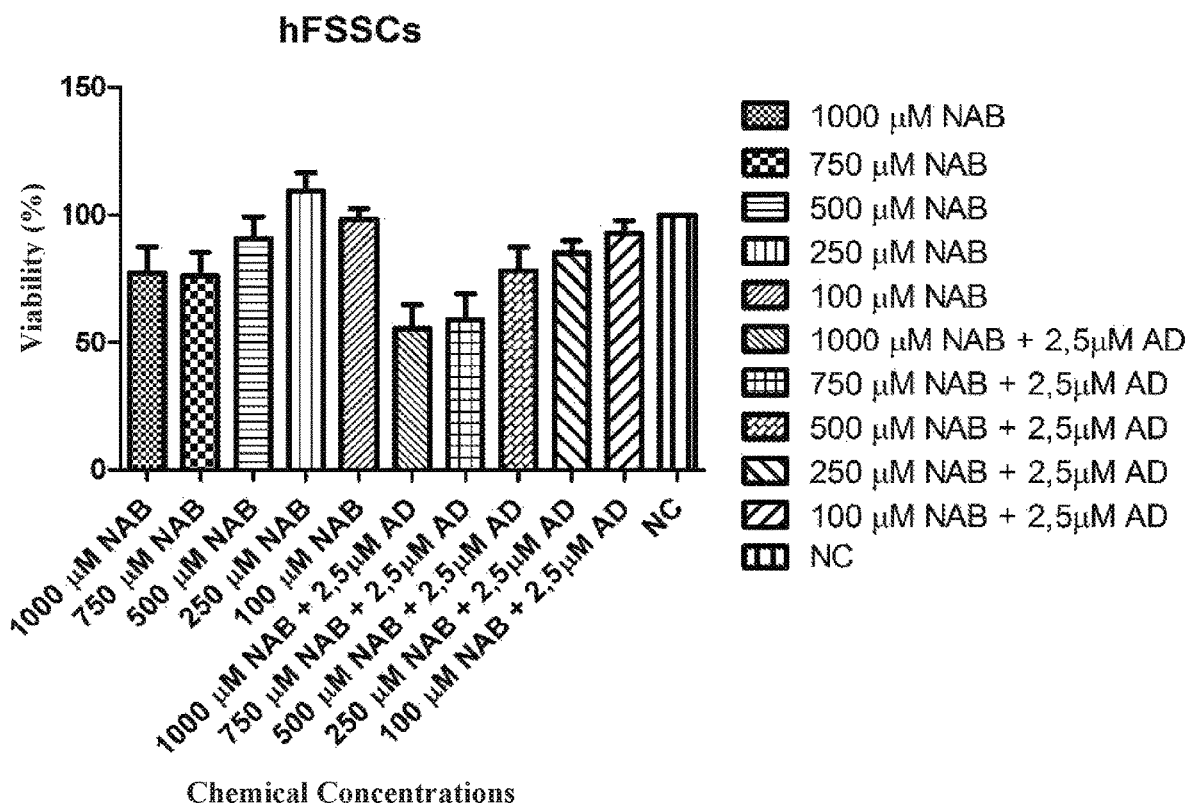

FIG. 2 shows the graph of the effect of NAB alone and in combination with AD at the end of 48-hour incubation on the cellular viability of healthy human foreskin stem cells (hFSSCs).

In the related graph, the viability profiles of healthy human foreskin stem cells (hFSSCs) were observed upon 48-hour of incubation with NAB alone and combination thereof with AD. In accordance with the obtained results, it was observed that the viability destroying effect of combination of 250 μM NAB and 2.5 μM AD on hFSSC cells was low (85% viability).

Figure 3:
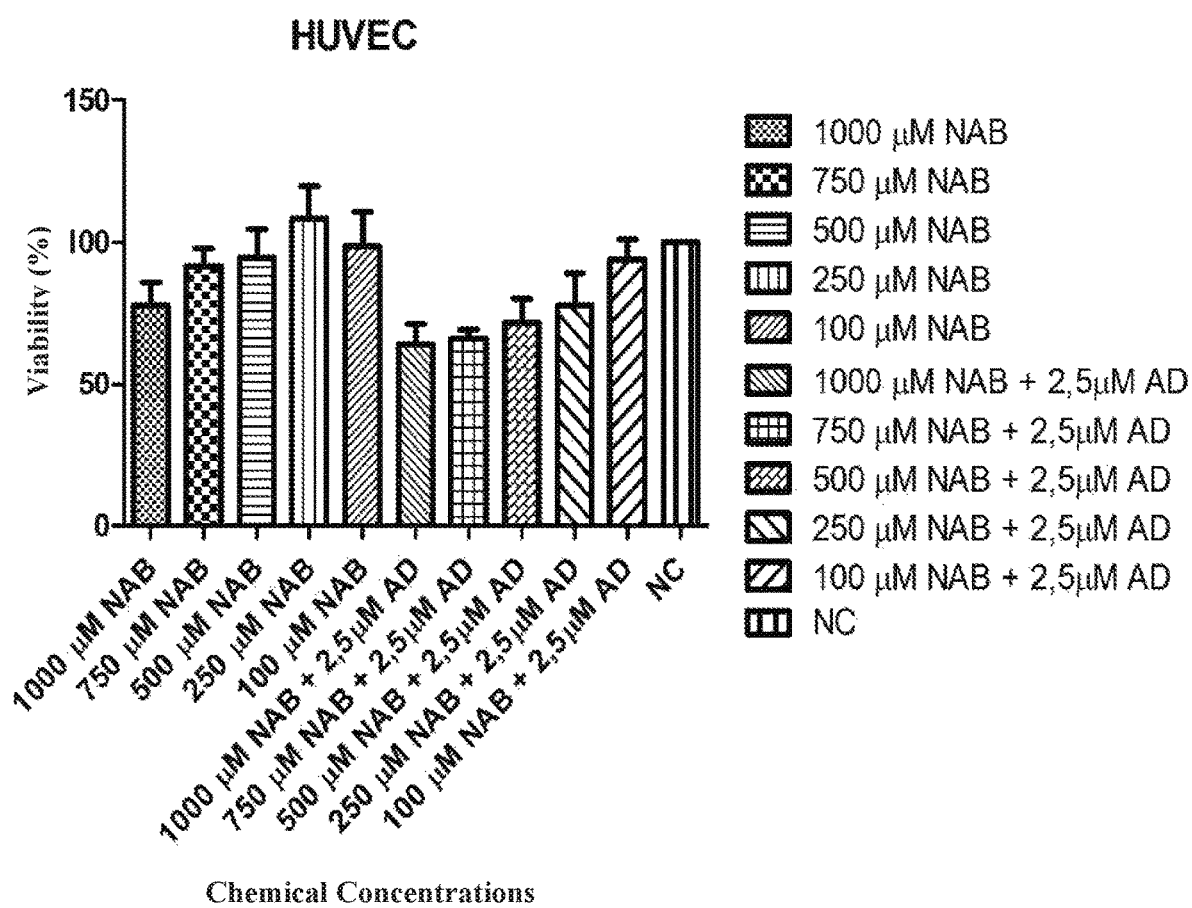

FIG. 3 shows the graph of the effect of NAB alone and in combination with AD at the end of 48-hour incubation on the viability of healthy human umbilical vein endothelial cell (HUVEC).

In the related graph, the viability profiles of healthy human umbilical vein endothelial cells were observed upon 48-hour of incubation with NAB alone and in combination with AD. In accordance with the obtained results, it was observed that the viability destroying effect of combination of 250 μM NAB and 2.5 μM AD on HUVEC cells was low (94% viability).

Figure 4:
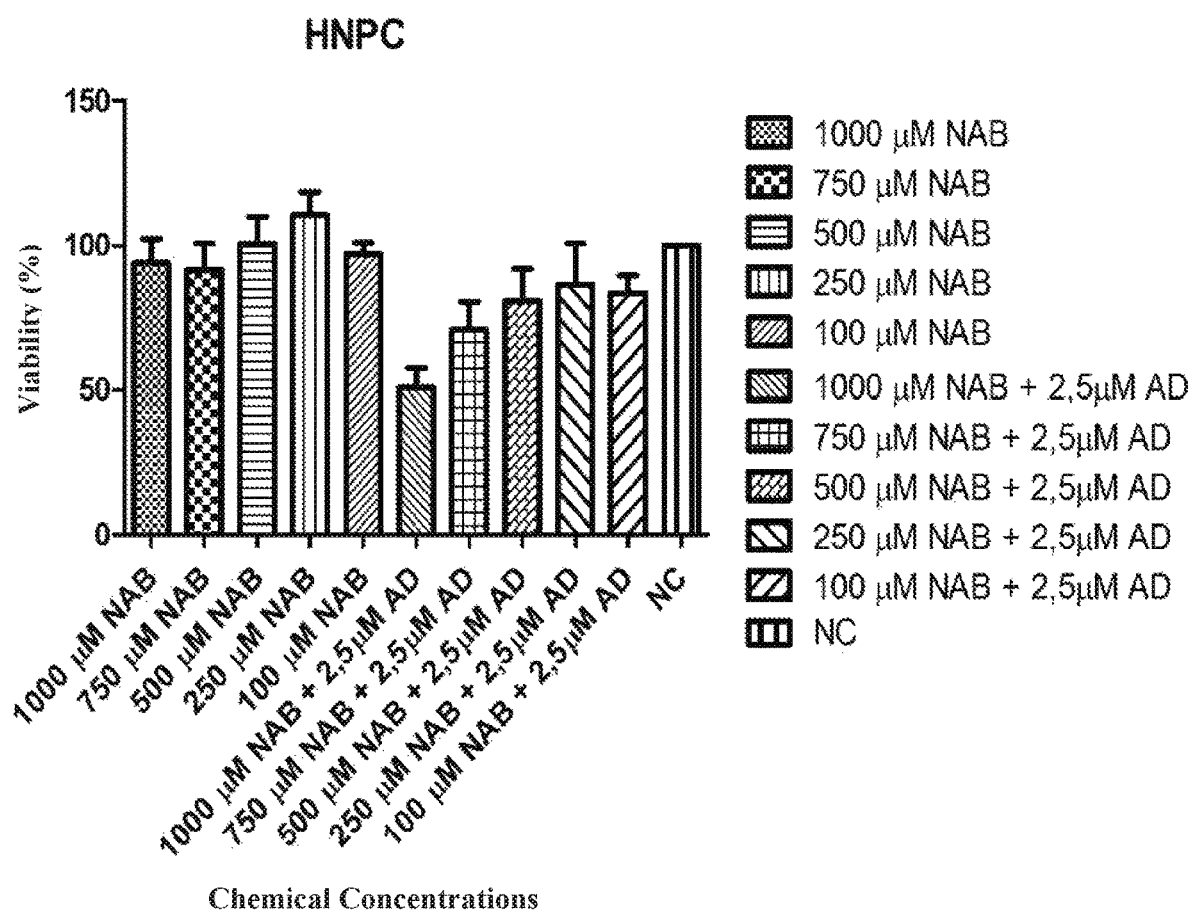

FIG. 4 shows the graph of the effect of NAB alone and in combination with AD at the end of 48-hour incubation on the viability of healthy intervertebral disc cell (HNPC).

In the related graph, the viability profiles of healthy intervertebral disc cell were observed as a result of 48-hour incubation of NAB alone and in combination with AD. In accordance with the obtained results, it was observed that the viability destroying effect of combination of 250 μM NAB and 2.5 μM AD on HNPC cells was low (86% viability).

Figure 5:
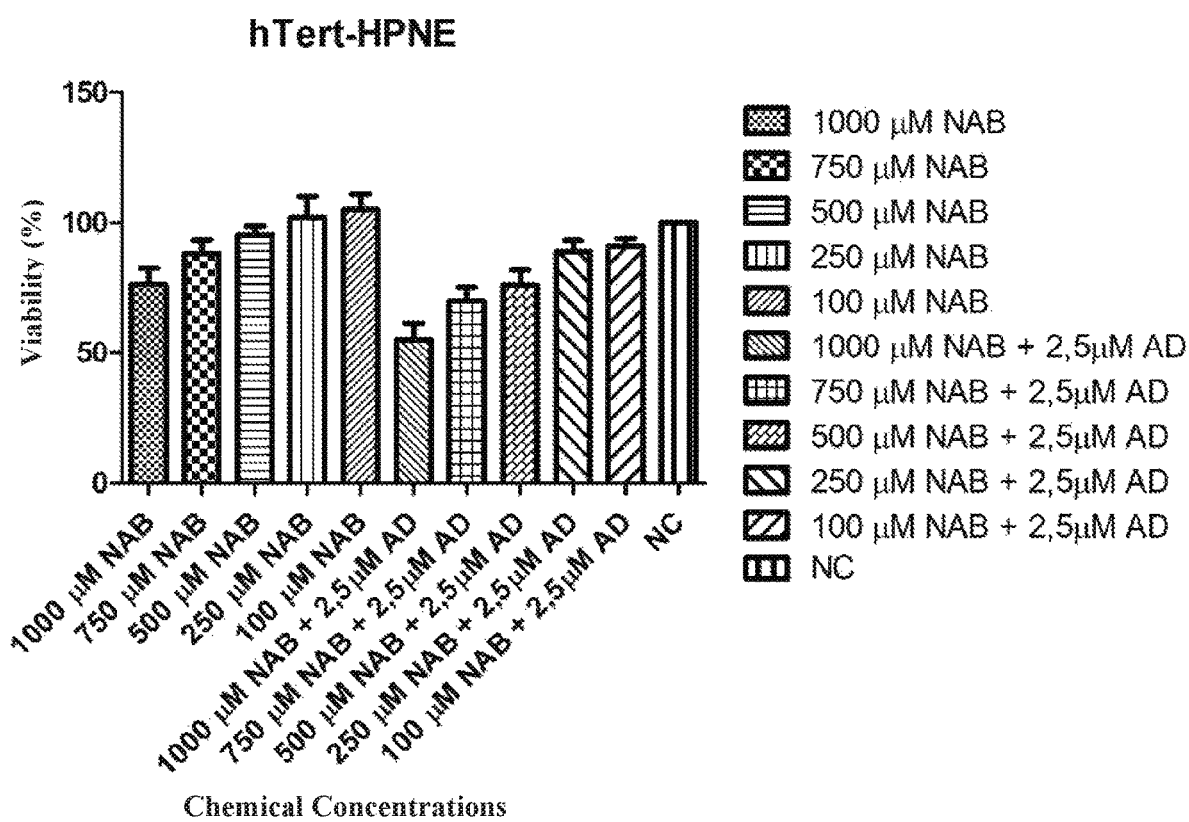

FIG. 5 shows the graph of the effect of NAB alone and in combination with AD at the end of 48-hour incubation on the viability of healthy human pancreatic cell (hTert-HPNE).

In the related graph, the viability profiles of healthy human pancreatic cell were observed as a result of 48-hour incubation of NAB alone and in combination with AD. In accordance with the obtained results, it was observed that the viability destroying effect of combination of 250 μM NAB and 2.5 μM AD on HNPC cells was low (89% viability).

As a result of the analysis performed on healthy cells with NAB alone and in combination with AD, it was determined that the dose to be used on healthy cells and cancer cells was the combination 250 μM NAB and 2.5 μM AD. This dose and the other doses used on healthy cells were injected on pancreatic cancer cells and their effects within a period of 48 hours were observed.

Figure 6:
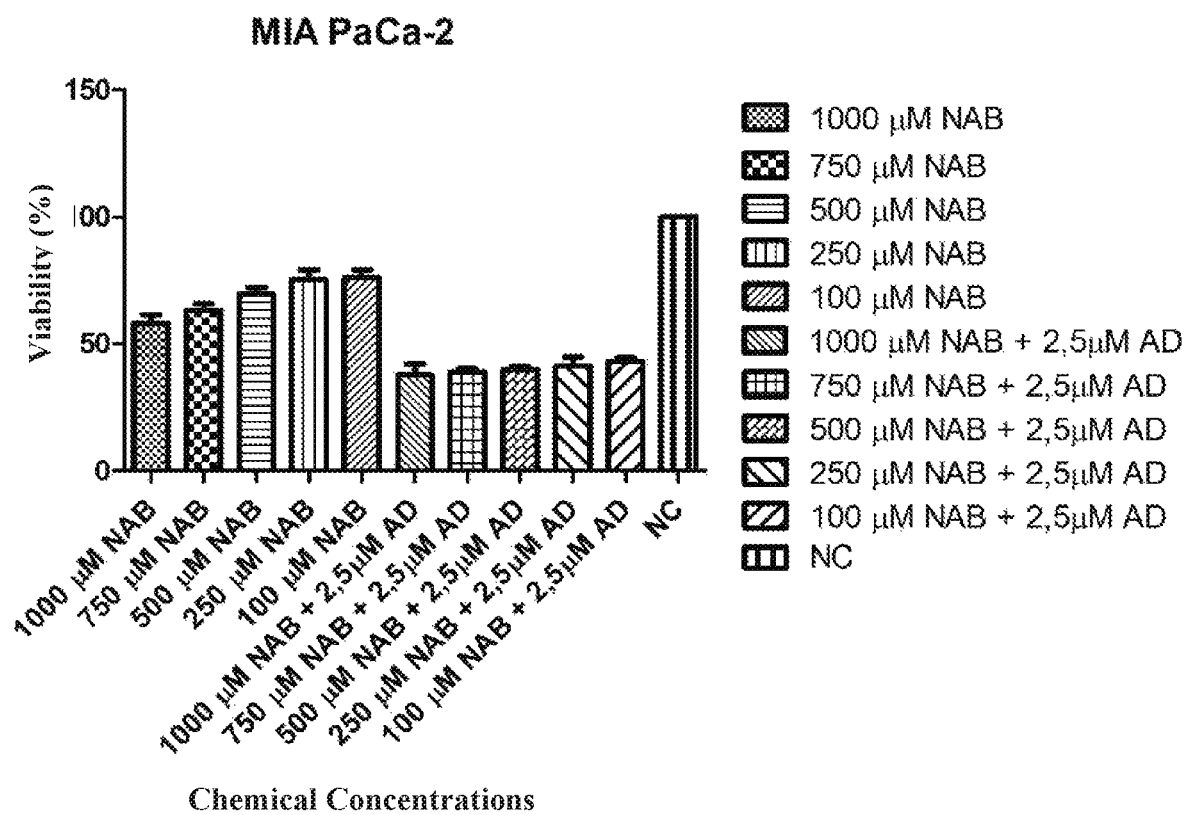

FIG. 6 shows the graph of the effect of NAB alone and in combination with AD at the end of 48-hour incubation on the viability of pancreatic cancer cell (MIA PaCa-2).

In the related graph, the viability profiles of pancreatic cancer cell (MIA PaCa-2) were observed as a result of 48-hour incubation of NAB alone and in combination with AD. In accordance with the obtained results, it was determined that the viability destroying effect of combination of 250 μM NAB and 2.5 μM AD on MIA PaCa-2 cells was higher than the effect of the same dose of AD alone (41%). While application of AD alone decreased viability of MIA PaCa-2 cells to 53%, when NAB and AD were applied in combination, an extra 12% decrease was observed in viability.

Figure 7:
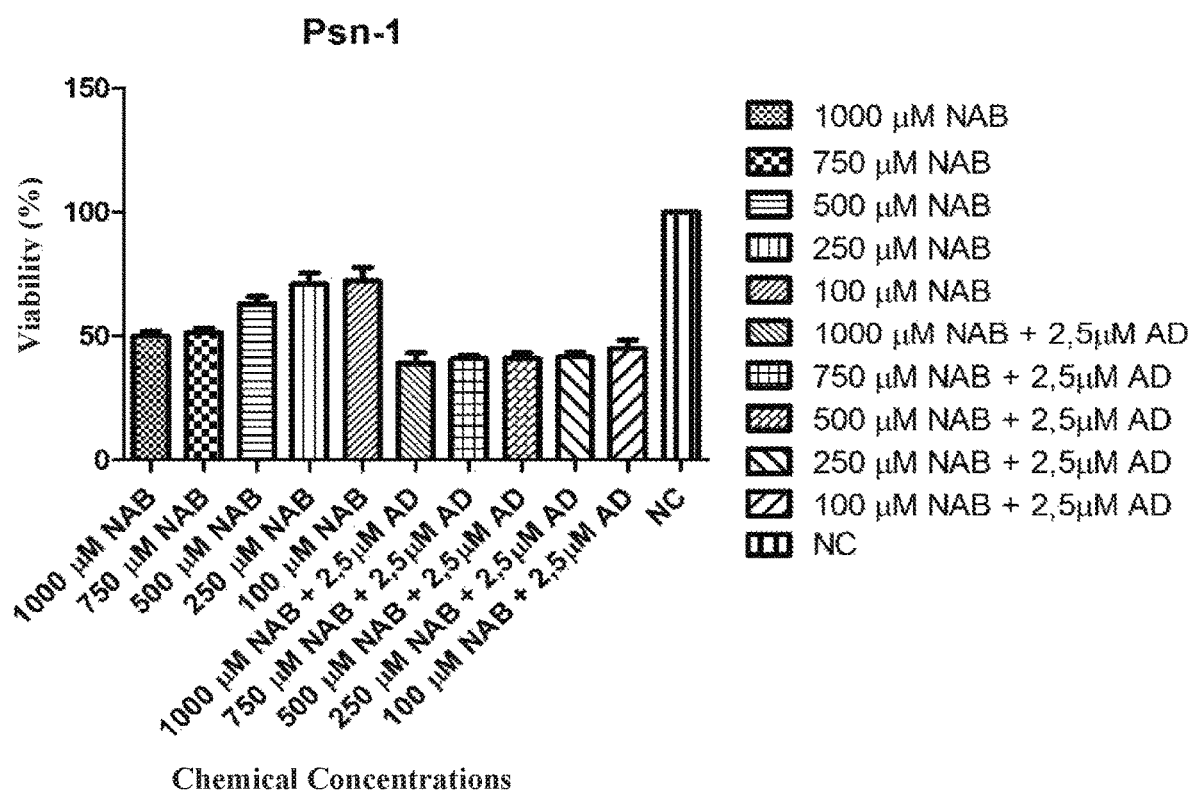

FIG. 7 shows the graph of the effect of NAB alone and in combination with AD at the end of 48-hour incubation on the viability of pancreatic cancer cell (Psn-1).

In the related graph, the viability profiles of pancreatic cancer cell (Psn-1) were observed as a result of 48-hour incubation of NAB alone and in combination with AD. In accordance with the obtained results, it was observed that the viability destroying effect of combination of 250 μM NAB and 2.5 μM AD on Psn-1 cells was higher than the effect of the same dose of AD alone (41.60%). While application of AD alone decreased viability of Psn-1 cells to 51.6%, when NAB and AD were applied in combination, an extra 10% decrease was observed in viability.

Figure 8:
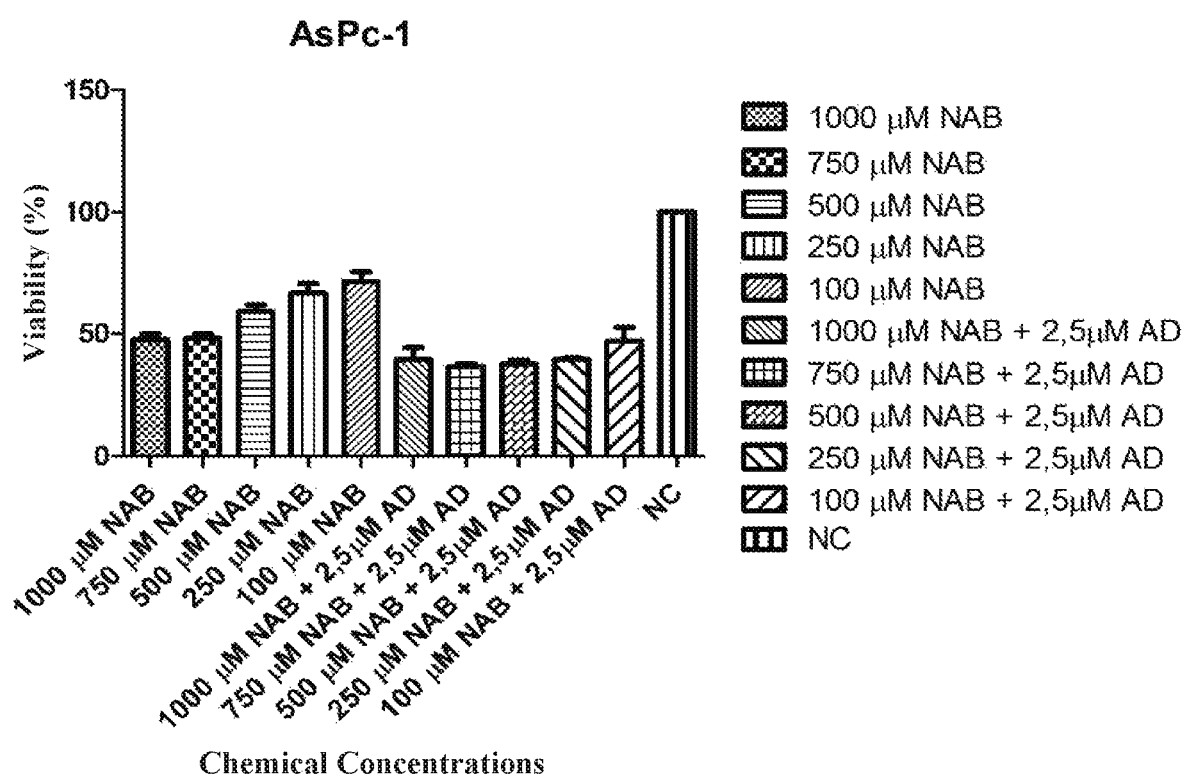

FIG. 8 shows the graph of the effect of NAB alone and in combination with AD at the end of 48-hour incubation on the viability of pancreatic cancer cell (AsPc-1).

In the related graph, the viability profiles of pancreatic cancer cell (AsPc-1) were observed as a result of 48-hour incubation of NAB alone and in combination with AD. In accordance with the obtained results, it was observed that the viability destroying effect of combination of 250 μM NAB and 2.5 μM AD on AsPc-1 cells was higher than the effect of the same dose of AD alone (39.2%). While application of AD alone decreased viability of AsPC-1 cells to 58.3%, when NAB and AD were applied in combination, an extra 19% decrease was observed in viability.

As a result of the analyses conducted, it was proved that alexidine dihydrochloride has chemotherapeutic activity on pancreatic cancer cells. It was found that by 2.5 μM of AD which is the median toxic dose (TD50) for pancreatic cancer cells do not kill the healthy cells. In the light of the information found, it can be used as a chemotherapeutic agent in pancreatic cancer treatment.

With the invention, a combination of alexidine dihydrochloride and sodium pentaborate pentahydrate can be obtained and used as a chemotherapeutic agent in the treatment of pancreatic cancer. With this combination, the viability of pancreatic cancer cells was reduced at least 10% more.

What is claimed is:

1. A chemotherapeutic agent comprising a combination of alexidine dihydrochloride compound and sodium pentaborate pentahydrate compound, wherein the chemotherapeutic agent is used for pancreatic cancer treatment,
   wherein a final concentration of the alexidine dihydrochloride compound is 2.5 μM and a final concentration of the sodium pentaborate pentahydrate compound is 250 μM.

2. The chemotherapeutic agent according to claim 1, wherein the chemotherapeutic agent is obtained by the steps of;
   weighing the alexidine dihydrochloride compound,
   adding dimethylsulfoxide compound therein and preparing a stock solution at a concentration of 10 μM,
   storing the stock solution at a temperature of −20° C. at an unilluminated environment until time of use,
   supplying a first sodium pentaborate pentahydrate solution and by dissolving the first sodium pentaborate pentahydrate solution in a medium, forming a second sodium pentaborate pentahydrate solution at a concentration of 1000 μM,
   diluting the second sodium pentaborate pentahydrate solution dissolved in the medium to a concentration of 250 μM to obtain a third sodium pentaborate pentahydrate solution,
   filtering and sterilizing the third sodium pentaborate pentahydrate solution diluted to the concentration of 250 μM, and
   adding the alexidine dihydrochloride compound into the third sodium pentaborate pentahydrate solution having the concentration of 250 μM to obtain a mixed solution with the final concentration of 2.5 μM for the alexidine dihydrochloride compound.

3. The chemotherapeutic agent according to claim 1, wherein the chemotherapeutic agent is stored for 72 hours at a temperature of 4° C. without a degradation.

4. The chemotherapeutic agent according to claim 1, wherein the chemotherapeutic agent decreases viability of pancreatic cancer cells by 60-80%, wherein the pancreatic cancer cells are selected from the group consisting of MIA PaCa-2, AsPc-1, and Psn-1.

5. The chemotherapeutic agent according to claim 1, wherein the chemotherapeutic agent decreases viability of healthy pancreatic cells of hTert-HPNE by 10-15%.

6. The chemotherapeutic agent according to claim 1, wherein the chemotherapeutic agent decreases viability of healthy intervertebral disc cells of HNPC by 10-15%.

7. The chemotherapeutic agent according to claim 1, wherein the chemotherapeutic agent decreases viability of human foreskin mesenchymal stem cells of hFSSCs by 10-15%.

8. The chemotherapeutic agent according to claim 1, wherein the chemotherapeutic agent decreases viability of healthy umbilical vein endothelial cells of HUVEC by 5-10%.

* * * * *